United States Patent [19]
Sandifer et al.

[11] Patent Number: 5,526,121
[45] Date of Patent: * Jun. 11, 1996

[54] VARIABLE FILTER SPECTROPHOTOMETERS

[75] Inventors: James R. Sandifer, Rochester; David S. Uerz, Ontario, both of N.Y.

[73] Assignee: Eastman Kodak Company, Rochester, N.Y.

[ * ] Notice: The term of this patent shall not extend beyond the expiration date of Pat. No. 5,386,295.

[21] Appl. No.: 5,320

[22] Filed: Jan. 15, 1993

Related U.S. Application Data

[63] Continuation-in-part of Ser. No. 951,607, Sep. 28, 1997, Pat. No. 5,357,343, which is a continuation of Ser. No. 737,824, Jul. 26, 1991, abandoned, which is a continuation-in-part of Ser. No. 591,204, Oct. 1, 1990, abandoned.

[51] Int. Cl.⁶ .............................. G01N 21/25; G01J 3/00
[52] U.S. Cl. ...................... 356/418; 356/419; 356/51; 250/351
[58] Field of Search ...................... 356/323, 319, 356/320, 321, 324, 325, 326, 414–416, 417, 418, 419, 420, 51; 250/351; 235/468

[56] References Cited

U.S. PATENT DOCUMENTS

| | | | |
|---|---|---|---|
| 3,780,299 | 12/1973 | Bock | 250/209 |
| 3,999,062 | 12/1976 | Demsky et al. | 250/227 |
| 4,061,428 | 12/1977 | Amano et al. | 356/175 |
| 4,097,743 | 6/1978 | Carlson | 250/339 |
| 4,291,985 | 9/1981 | Tsujimura | 356/408 |
| 4,305,663 | 12/1981 | Perkins et al. | 356/323 |
| 4,392,056 | 7/1983 | Weyandt | 235/468 X |
| 4,477,190 | 10/1984 | Liston et al. | 356/418 |
| 4,644,485 | 2/1987 | Ferber et al. | 364/569 |
| 4,648,714 | 3/1987 | Benner et al. | 356/301 |
| 4,945,250 | 7/1990 | Bowen et al. | 250/461.1 |
| 5,267,178 | 1/1993 | Berner | 356/319 X |

FOREIGN PATENT DOCUMENTS

| | | | |
|---|---|---|---|
| 479379A | 4/1992 | European Pat. Off. | 356/323 |
| 291855A5 | 7/1991 | Germany. | |

OTHER PUBLICATIONS

"In–Situ Measurement", IEEE Transactions, Jul. 1975, Konnerth et al.
Wetzel, D. L., "Near–Infrared Reflectance Analysis", Anal. Chem., 55(1983)1165A.
Stinson, S. C., "Advances Made in Applying IR Sensors to Process Control", Chem. and Eng. News, Jan. 1989, p. 30.

(List continued on next page.)

Primary Examiner—Vincent P. McGraw
Assistant Examiner—K. P. Hantis
Attorney, Agent, or Firm—Susan L. Parulski

[57] ABSTRACT

A variable filter spectrophotometer, for use with sample and reference; has a main member, a filter unit, a drive, a detector, a light distribution system, and a clamping circuit. The main member defines first and second beam paths, which are intersected by the filter unit. The filter unit has filtering and opaque portions. The filter unit is continuously movable relative to the beam paths in a repeating cycle from a first filtering relation in which the filtering portion is interposed in the first beam path and the opaque portion completely blocks the second beam path, to a first dark relation in which both beam paths are blocked, to a second filtering relation in which the filtering portion is interposed in the second beam path and the first beam path is completely blocked, and to a second dark relation in which both beam paths are completely blocked. The filtering portion is variably transmissive along a direction of movement of the filter unit. The drive continuously moves the filter unit relative to the beam paths. The detector produces a signal responsive to light received. The light distribution system directs light separately to and from the sample and reference, to and from the beam paths, and to the detector. The clamping circuit clamps the signal produced by the detector during the filtering relations to the signal produced by the detector during the dark relations.

19 Claims, 9 Drawing Sheets

OTHER PUBLICATIONS

P. Dubois et al., "Determination of Five Components in a Pharmaceutical Formulation Using Near Infrared Reflectance Spectrophotometers", Analyst, vol. 112, p. 1675 (1987).

B. R. Buchanan et al., "Detection of Ethanol in Wines Using Optical–Fiber Measurements and Near–Infrared Analysis", Appl. Spect., vol. 42, p. 1106 (1988).

Instruction Manual, Microquad 8000, Nov. 25, 1984.

Konnerth, K. L. "IOTA, a New Computer Controlled Thin Film Thickness Measurement Tool", 1972, vol. 15, pp. 271–380.

Hansen, G. L., "Introduction to Solid–State Television Systems, Color and Black & White", pp. 128–131.

Whalen, A. D., Detection of Signals in Noise, 1971, pp. 238–241.

Optical Coating Laboratory, Inc., Stock Filter Catalog, 1990–1991.

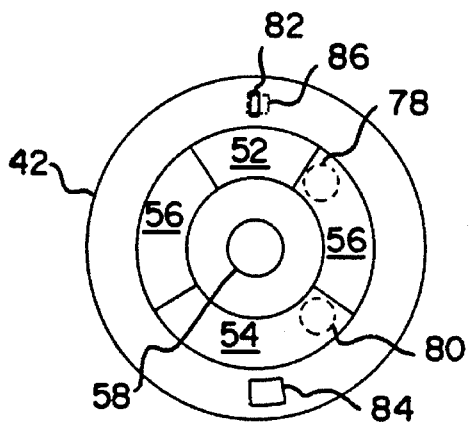
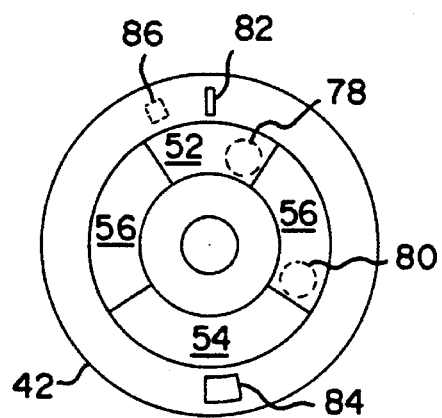
FIG. 6　　　　FIG. 7
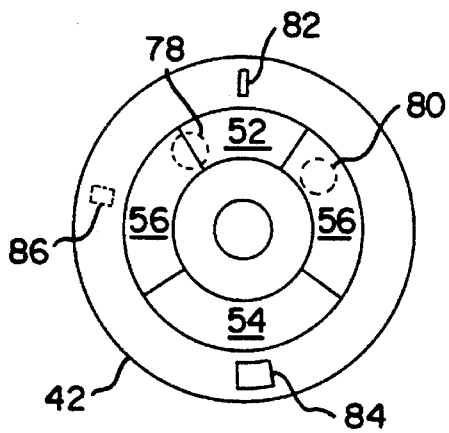
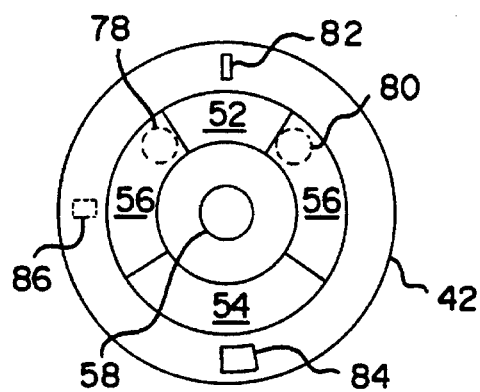
FIG. 8　　　　FIG. 9
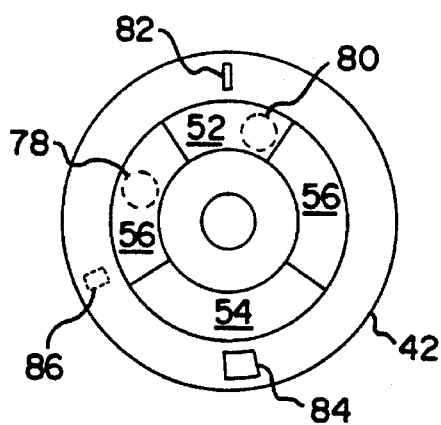
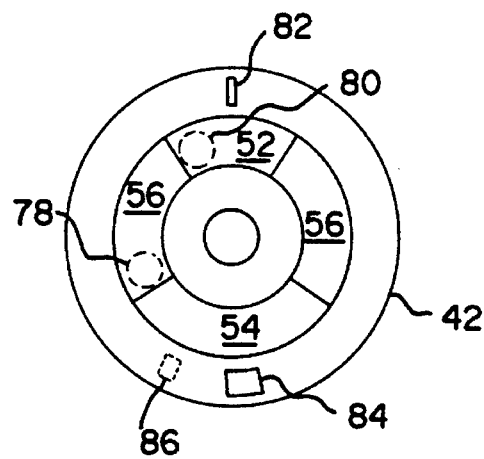
FIG. 10　　　　FIG. 11

VARIABLE FILTER SPECTROPHOTOMETERS

CROSS REFERENCE TO RELATED APPLICATIONS

This application is a continuation-in-part of commonly assigned, and allowed application Ser. No. 07/951,607 now U.S. Pat. No. 5,357,343 filed 28 Sept. 1992 by the present applicants, Alan J. Lowne, Steven C. Switalski and Hsue-Yang Liu; which is a continuation of Ser. No. 07/737,824 filed 26 Jul. 1991 and now abandoned; which was a continuation-in-part of Ser. No. 07/591.204 filed 1 Oct. 1990 and now abandoned.

FIELD OF THE INVENTION

The present invention relates to spectrophotometry and spectrophotometers and more particularly relates to variable filter spectrophotometric devices and to spectrophotometers incorporating such devices.

BACKGROUND OF THE INVENTION

Photometers are known that use a single light source, a single detector and "dual beam" fiber optics that split the light into a reference beam and a sample beam. Such a device is shown, for example, in U.S. Pat. No. 4,061,428, in which a chopper wheel has equal numbers of apertured portions for a reference beam and a sample beam to pass through a selected filter in the aperture. The angular placement of the apertures is the same as such placement of the bifurcated fiber optics. As a result, the only way to prevent both the sample beam and the reference beam from arriving at the detector simultaneously (an unacceptable result), is to position an oscillating shutter adjacent to the chopper. (Although there are also additional apertures in the chopper, these are used to detect red versus green versus blue filters, and do not control whether a reference beam or a sample beam is in place). Such a use of a chopper and a shutter has a decided disadvantage, there are at least two moving parts required, each of which is subject to wear and risk of breakdown.

Konnerth et al, "In-Situ Measurement", IEEE Transactions (7/75) teaches a spectrophotometer in which there appears to be only one moving part. In that case, a triggering mechanism would not be used to inform the computer as to the location of the chopper. A highly accurate and expensive motor would, however, be required since the timing of chopper rotation would have to be exact.

U.S. Pat. No. 4,648,714 teaches a dual beam spectrophotometer having a single moving part, however, it does this at the expense of two detectors for reference and sample. The use of two different detectors is well known to be a source of drift error.

U.S. Pat. No. 4,097,743 teaches an optical system for a moisture analyzer in which two light beams are reflected at locations 180 degrees apart on a rotary wheel. The wheel has two filters and a window, all equally spaced 120 degrees apart. A series of mirrors are attached to the wheel at fixed positions, and provide signals to a sensor indicating wheel positions. Outputs are produced by the analyzer in the form of two time related pulse trains: a train of spaced pulses representing individual signals from each beam-filter combination and a train of periodic commutator pulses identifying wheel positions including a home position. The momentary pulses are used by a decoder circuit to separate the other pulse train, after amplification, into separate signals representing the beam-filter combinations. At the home position, a portion of the detection circuit is grounded, apparently providing an electronic "dark" signal. The decoded signals are combined, along with a reference voltage to provide a voltage representing sample moisture content which is displayed. This device has the shortcoming that detector related "noise", such as dark current, is not corrected for, in that the electronic "dark" signal is exclusive of the detector, which is grounded, regardless of whether or not residual photocurrent is flowing.

Some previous Raman spectrometers have used filters to attempt to provide a simpler instrument. U.S. Pat. No. 4,586,819 teaches the use of a filter wheel with a laser and a monochromator. The filter wheel is used at an angle to the excitation laser beam and to the returning scattered Raman and laser signals from the sample. The device uses a laser oscillator to change the wavelength of the excitation beam. The function of the filters is to allow the reflected laser beam to pass on to a camera, and also to reflect the Raman scatter into a monochromator. The monochromator is used to select the Raman frequencies. Therefore, the filter wheel functions as a variable blocking filter, preventing the laser beam from entering the monochromator. The instrument does not have a reference beam, and the light is not modulated. The monochromator, not the filter wheel, provides the frequency discrimination to obtain a Raman spectrum.

U.S. Pat. No. 4,648,714 teaches the use of a rotating filter wheel to select Raman frequencies to detect respiratory and anesthesia gases with one detector. The filter wheel serves only to provide a selection of Raman frequencies. A black filter is provided in the filter wheel for referencing the dark signal of the detector.

U.S. Pat. No. 4,784,486 is a Raman spectrometer in which multiple detectors and associated interference filters are used instead of a filter wheel to select Raman frequencies. This greatly complicates the device, and would not provide the advantages of stability and low cost sought for many applications.

Some luminescence spectrometers have used filters to provide a simple instrument. U.S. Pat. No. 3,999,062 uses a circular variable filter and a light path divided into a sample and a reference beam to provide an instrument to measure the amount of fluorescence. The instrument loops the light beams back through the filter wheel for a second pass, reducing the amount of space useful for wavelength selection. The wheel is designed such that a dark signal is not obtained. The main function of the device is to alternate between polychromatic and monochromatic excitation. This complexity requires a particular design for the light paths and a particular method to analyze the signal information, but does not lend itself to the purpose of providing an simpler instrument for general emission spectroscopy.

U.S. Pat. No. 4,477,190 teaches the use of two filter wheels that are synchronously rotated to provide light to multiple samples: the resultant light outputs from the samples are directed to multiple detectors. Although this provides a multichannel spectrophotometer, it does not provide a simple spectrometer, nor does it provide these capabilities from a single moving part.

U.S. Pat. No. 4,945,250 and 4,977,325 teaches the use of a filter wheel for a UV fluorescence spectrometer. It uses pairs of filters, thereby reducing the available space on the filter wheel for selection. Additionally, two detectors are used, incorporating an additional source of drift. The geometry of the housing is specifically designed for this filter wheel, and does not provide for a flexible modulating, switching, and wavelength selection component for luminescence spectroscopy.

It is therefore desirable to provide a spectrophotometer which has dual sample and reference beams and a variable filter, and which corrects for unwanted signal, requires only a single moving part, and is relatively rugged, and stable.

SUMMARY OF THE INVENTION

In the broader aspects of the invention, there is provided a variable filter spectrophotometer, for use with sample and reference; has a main member, a filter unit, a drive, a detector, a light distribution system, and a clamping circuit. The main member defines first and second beam paths, which are intersected by the filter unit. The filter unit has filtering and opaque portions. The filter unit is continuously movable relative to the beam paths in a repeating cycle from a first filtering relation in which the filtering portion is interposed in the first beam path and the opaque portion completely blocks the second beam path, to a first dark relation in which both beam paths are blocked, to a second filtering relation in which the filtering portion is interposed in the second beam path and the first beam path is completely blocked, and to a second dark relation in which both beam paths are completely blocked. The filtering portion is variably transmissive along a direction of movement of the filter unit. The drive continuously moves the filter unit relative to the beam paths. The detector produces a signal responsive to light received. The light distribution system directs light separately to and from the sample and reference, to and from the beam paths, and to the detector. The clamping circuit clamps the signal produced by the detector during the filtering relations to the signal produced by the detector during the dark relations.

It is an advantageous effect of at least some of the embodiments of the invention that a varied spectrum of wavelengths is provided in an apparatus which requires a single moving part and can use one light source and one detector.

BRIEF DESCRIPTION OF THE DRAWINGS

The above-mentioned and other features and objects of this invention and the manner of attaining them will become more apparent and the invention itself will be better understood by reference to the following description of an embodiment of the invention taken in conjunction with the accompanying drawings wherein:

FIGS. 6 to 13 are schematic section views of a portion of an alternative embodiment of the spectrophotometric device of the invention, taken generally through the axis of rotation of the filter unit; shown at eight different stages during a cycle of rotation of the filter unit. For clarity, the sample and reference beam paths and reader, indicated by dashed lines, are shown as rotating relative to a fixed filter unit.

DESCRIPTION OF PARTICULAR EMBODIMENTS

Figure 1:
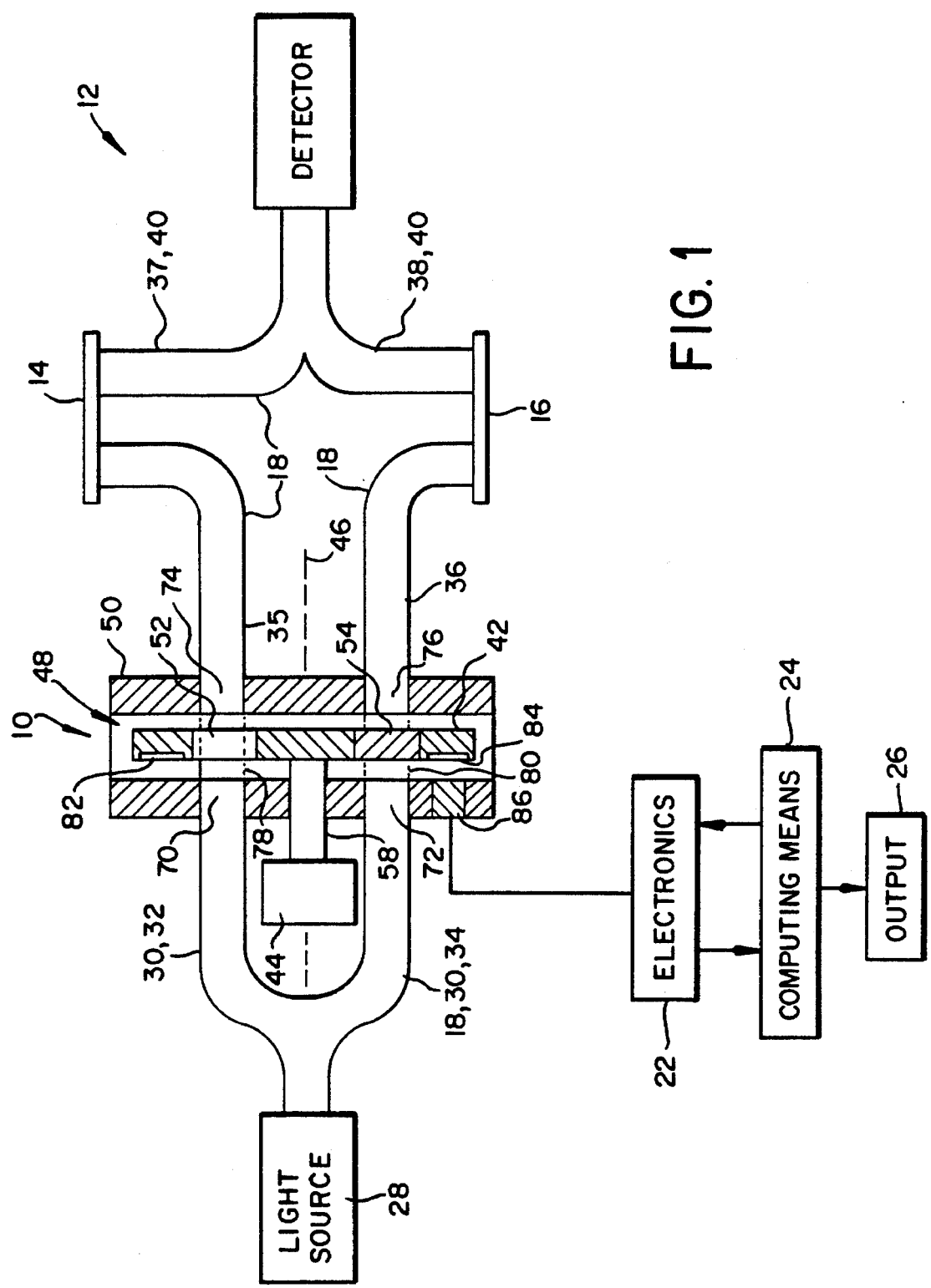
FIG. 1 is a schematic view of the overall construction of an embodiment of the spectrophotometer of the invention, shown at the stage when the sample is being illuminated.
Figure 2:
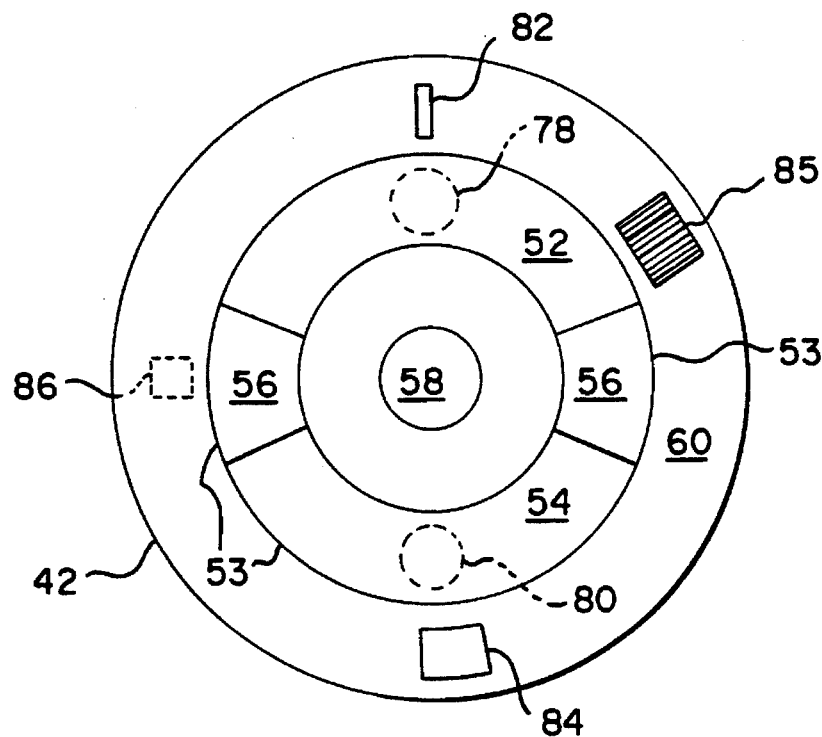
FIG. 2 is a schematic section view of a portion of the spectrophotometric device of the spectrophotometer of FIG. 1, taken generally through the axis of rotation of the filter unit, shown at the stage when the reference is being illuminated. The sample and reference beam paths and reader are indicated by dashed lines.

Referring to FIGS. 1 and 2, the spectrophotometer 12 of the invention has an optical path system 18, a detector 20, associated electronics 22, computing means 24, an output device 26, and the spectrophotometric device 10 of the invention and generally includes a light source 28.

Light source 28 is selected to provide a light beam having a suitable wavelength range for an intended use. Particular embodiments of the invention have usable wavelength ranges within 200 to 2800 nm, that is, ultraviolet through the near infrared. Light sources suitable for particular embodiments include gas, excimer, dye, solid-state, and diode lasers; tungsten, tungsten-halogen, xenon, and deuterium lamps; and solid-state emitters, such as light emitting diodes, doped optical fibers, and doped substances.

Optical path system 18 includes single optical fibers or fiber bundles which direct, split, and recombine the light beam, and may include auxilary filters which provide non-varying filtration of the beam. As a matter of convenience, the terms "fiber" and "optical fiber" are used hereafter to designate both individual fibers and bundles of fibers. Fibers and light source are selected to meet the requirements of a particular embodiment of the invention while avoiding excessive attenuation and other degradation of the light transmitted. In a Raman spectrophotometer 12, for example, strong fluorescence within a fiber leading to the sample and reference is deleterious. Low fluorescence optical fibers such as Si/Ge fibers can be used to avoid this problem. Alternatively, an infrared light source at, for example, 780, 830, 980, or 1064 nm, can be used to achieve the same result with Si fibers.

Optical path system 18 has an entry fiber 30, which receives the light beam from light source 28 and, dividing into sample and reference arms 32,34, respectively, directs sample and reference beam portions to spectrophotometric device 10.

Sample and reference intermediate fibers 35,36, respectively, deliver respective beam portions to sample 14 and reference 16. Sample and reference arms 37,38, respectively of exit fiber 40 receive scattered and emitted light from reference 16 and sample 14 and, recombine the light for delivery to detector 20.

FIG. 1 illustrates optical path system 18 schematically. The geometry of the various fibers can be modified, for example, by the use of fiber optic probes, such as bifurcated random bundles or bundles with particular geometries to enhance signal collection such as excitation fibers in different orientations with collection fibers, gradient index and refractive lenses, and other optical elements such as mirrors, to change beam size, shape, and direction.

The geometry of optical path system 18 can be modified to meet the needs of a particular use. Respective light beams can be directed through or reflected from sample 14 and reference 16. Optical path system 18 may or may not include holders (not specifically illustrated) for sample and reference materials, depending upon the nature of the sample 14 and reference 16. The sample can be gas, liquid, or solid, including tissue, textiles, powders, pharmaceuticals, tablets, sheets, and chemical analytes in various forms. The reference can be a "standard", that is, a substance or configuration of substances that has an invariant composition with regard to the type of spectroscopy performed and can provide a signal at appropriate wavelengths. Such a standard could be a liquid, solid, or gas that has been encapsulated to prevent degradation by the environment (for example, for a Raman standard: a glass vial of an inorganic salt, such as potassium nitrate, that has been purified and sealed under vacuum). Such a standard could also include the optical components of the reference arm 36 itself.

The spectrophotometer 12 of the invention is useful for both conventional spectroscopy in which sample and reference beams are transmitted through spectrophotometric device 10 before transmission to a sample and a reference and to other types of spectroscopy in which the beams are transmitted to the sample and reference first. Such forms of spectroscopy include scattering and emission spectroscopy. Examples of forms of scattering spectroscopy are normal Raman spectroscopy, surface enhanced Raman spectroscopy, anti-Stokes Raman spectroscopy, and resonance Raman spectroscopy. Examples of emission spectroscopy are fluorescence, phosphorescence, chemiluminescence, and bioluminescence.

Figure 4:
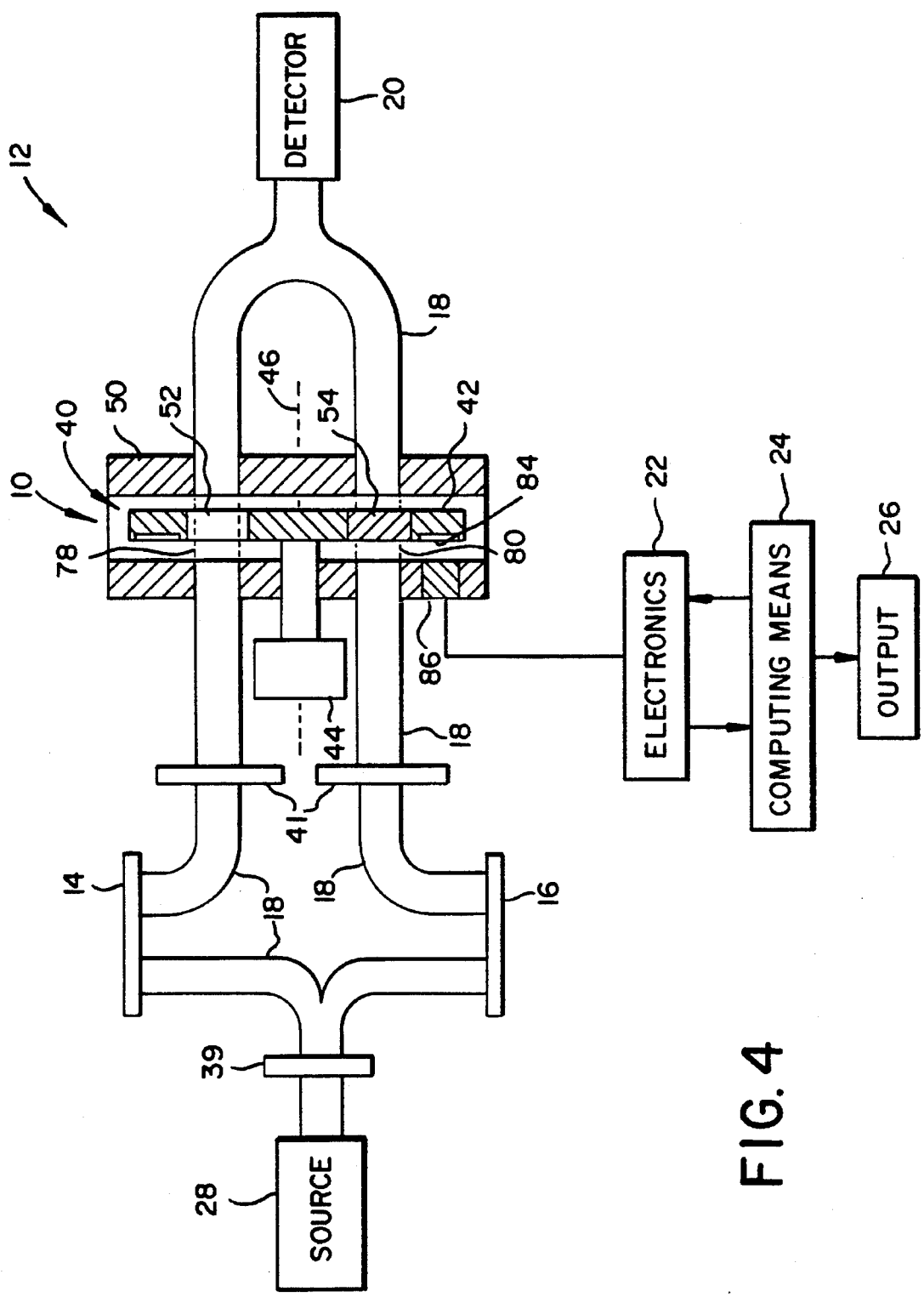
FIG. 4 is a schematic view of the overall construction of another alternative embodiment of the spectrophotometer of the invention, shown at the stage when the sample is being illuminated.
Figure 12:
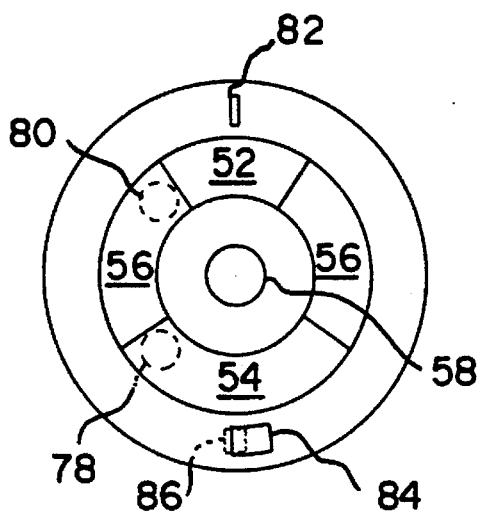
Figure 13:
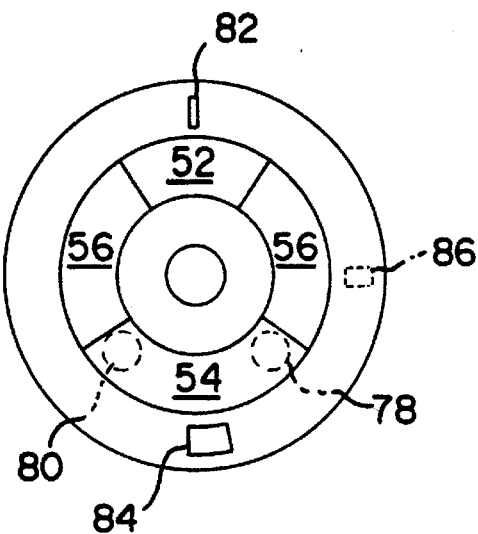

An example of a Raman spectrophotometer 12 is shown in FIG. 4. In this device 12, light source 28 is a laser or other monochromatic light source such as, for example, a 25 mW helium-neon laser that emits at 632.8 nm and the light beam in entry fiber 30 is first directed through a preconditioning filter 39 to remove unwanted wavelengths. Preconditioning filter 39 is a laser line interference filter, designed to pass only the laser line and prevent other wavelengths including the plasma lines of the helium-neon laser from passing. Light from sample 14 and reference 16 is directed through conditioning filters 41 to remove extraneous portions of the beam. Conditioning filters 41 are complementary to preconditioning filter 39, that is, conditioning filters 41 remove all the intensity at those wavelengths that were allowed to pass to the reference 16 and sample 14 by preconditioning filter 39, in this case, the source excitation wavelength. In the Raman spectrophotometer 12 shown in FIG. 4, reference 16 is a reflective substrate, such as a mirror, or a diffusely reflective substrate, such as an alumina ceramic plate or the like. The Raman spectrophotometer 12 can be further modified to include an optical fiber or a glass lens in which appropriate Raman lines can be excited. A separate attenuator, such as a neutral density filter, can be included to reduce the level of the reference beam or the reference 16 itself can provide attenuation to balance the level of the reference beam.

In another embodiment of spectrophotometer 12 in which phosphorescence is monitored, conditioning filters 41 reduce fluorescent light to permit easier measurement of wavelengths with phosphorescence intensity.

In embodiments of spectrophotometer 12 configured for use with self-luminescent sample 14 and reference 16, light source 28, entry fiber 30, and preconditioning filter 39 are unneeded if it is unecessary to change the luminescence signal.

Optical fibers 30,35,36,40 can be replaced by air paths and mirrors and can be otherwise varied to meet the requirements of a particular spectrophotometer 12.

Referring now to FIGS. 1 and 2, spectrophotometer 12 has a main member 50 which has an internal chamber 48. A filter unit 42 is mounted within in chamber 48 and rotates about an axis 46 defined by main member 50. Main member 50 has a pair of sides 68, which have pairs of opposed passages to which entry fiber branches 32,34 and intermediate fibers 35,36 are fixed at fiber ends 70,72 and 74,76, respectively. Entry fiber sample and reference branch ends 70,72 are aligned with sample and reference intermediate fibers 74,76, all respectively. Ends 70,72,74,76, desireably, include end elements (not shown) which function as wave guides, such as quartz rods or GRIN lenses. Pairs of opposed fiber ends 70,74 and 72,76 and respective passages in main member 50, define a pair of beam paths 78,80 through chamber 48.

Referring now to FIG. 2, filter unit 42 has a filtering portion 52 and an opaque portion 53, which together form an annular ring. Radially offset from filtering and opaque portions 52,53; filter unit 42 has an annular orientation section 60. Filter unit 42 and main member 50 are configured such that the annular ring of filtering and opaque portions 52,53 intersects the beam path pair 78,80. The relative size of filtering portion 52 can be maximized if the beam path pair 78,80 are 180 degrees apart, in which case dark portions 56 can be limited to arcs only large enough to accommodate beam paths 78,80; that is, the larger of beam paths 78,80 has a maximum dimension in the direction of travel of filter unit 42, which is about the same as the corresponding dimension of dark portions 56 in the direction of travel of filter unit 42 and at the same radial offset from axis 46. This relationship can also be stated in geometric terms. The arcs defined by dark portions 56 would have a circumferential dimension about equal to the maximum circumferential dimension of the larger of beam paths 78,80 at the same radial offset from axis 46. Restated another way, the arcs of each dark portion 56 would have about equal angular dimensions with the arc defined by a pair of radii which extend outward from axis 46 and are tangent to opposite sides of the larger of beam paths 78,80.

Filtering portion 52 is variably transmissive to selected wavelengths of light along a direction of movement of filter unit 42. The filtration varies along the arc of filtering portion 52. For example, filtering portion 52 can be a continuously variable filter or can have transmissiveness varied in steps.

Figure 5:
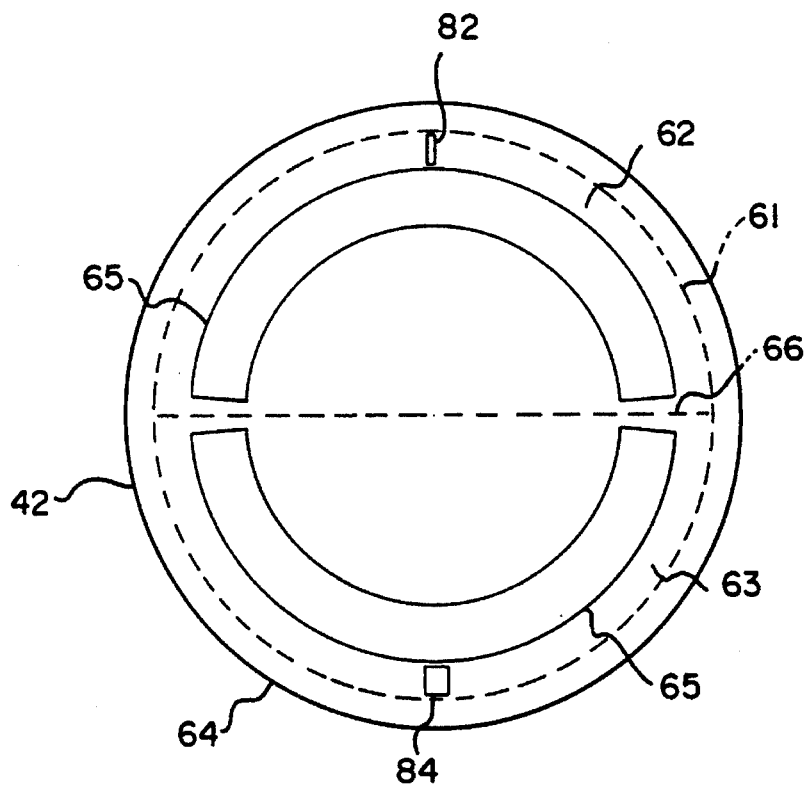
FIG. 5 is a front plan view of the filter unit of still another alternative embodiment of the invention.

Opaque portion 53 is at least substantially opaque to the the light transmittable by filtering portion 52. Desirably, opaque portion 53 is completely opaque. Opaque portion 53 can be further divided, on a functional basis, into blocking and dark portions 54,56, which are discussed below in greater detail. The embodiment of spectrophotometric device 10 shown in FIGS. 1 and 2 has a pair of dark portions 56 and a single blocking portion 54. In this embodiment, the maximum angular dimension of filtering portion 52 in the direction of movement of filter unit 42 is equal to the maximum angular dimension of blocking portion 54. Filtering, blocking and dark portions 52,54,56 are shown in FIG. 2 as discrete areas of filter unit 42, however, blocking and dark portions 54,56 can be continuous with each other and the remainder of filter unit 42. In such an embodiment of the invention, filtering portion 52, can be a filter inset within a solid disk. Filtering unit 42 can have a variety of other configurations, for example, FIG. 5 shows a multiple piece filter unit 42, in which a unitary disk 61, (indicated by dashed lines) having a hemicircular filter 62 and a hemicircular solid section 63, is fixed within a shell 64 having a pair of arc shaped slots 65. The slots 65 are separated by necks 66.

Referring again to FIGS. 1 and 2, filter unit 42 is joined to the shaft 58 of a motor 44, which is coaxial with filter unit 42 and main member 50 and rotates filter unit 42 relative to beam paths 78,80. Motor 44 drives filter unit 42 on a continuous rather than a stepwise basis. A wide variety of motors 44 could be used, however, stepper motors or the like would generally be non-optimal since they are not designed to operate continuously and might be subject to early failure in use in a continuous mode in the spectrophotometer of the invention. The speed of motor 44 is largely a matter of design choice, taking into account the limitations imposed by component strength, detector response time and the like.

Rotation of filter unit 42 relative to beam paths 78,80 is illustrated by FIGS. 6 to 13, for an alternative embodiment of spectrophotometric device 10 in which beam paths 78,80 have a center to center angular separation of ninety degrees. The position of beam paths 78,80 is indicated by dashed lines and the direction of rotation is counterclockwise. In FIG. 6, the leading periphery of sample beam path 78 is at the initial edge of filtering portion 52. As filter unit 42 continues to rotate, illustrated by FIGS. 7 and 8, filtering portion 52 travels through sample beam path 78. At the same time, blocking portion 54 travels through, and completely blocks, reference beam path 80. In the embodiment of the invention shown in FIGS. 6 to 13, a pair of dark portions 56 adjoin either side of filtering portion 52. In this embodiment of the invention, the maximum angular dimension of a blocking portion 54 is equal to or slightly larger than the minimum angular dimension from the leading periphery of sample beam path 78 to the trailing periphery of reference beam path 80, (this is most easily seen in FIG. 6 and 11), which is equal to the center to center angular separation of beam paths 78,80. Filtering portion 52 defines an arc having an angular dimension equal to or less than the angular separation of beam paths 78,80 from periphery to periphery. This is most easily seen in FIG. 9. In this embodiment, each blocking portion and the center to center angular separation of beam paths 78,80, each define an angle of 90 degrees, each beam path defines an arc of 23 degrees, filtering portion defines an arc of about 67 degrees, and dark portion defines an arc of 113 degrees.

As filter unit 42 is rotated about axis 46 by motor 44, beams are transmitted in the repeating cycle: sample beam only, both beams completed blocked, reference beam only, both beams completely blocked. When one beam path 78,80 is transmitted by filtering portion 52, the other beam path 80,78 is interrupted by a blocking portion 54. When one beam path 78,80 is interrupted by dark portion 56, the other beam path 80,78 is also interrupted.

Spectrophotometer 12 is described herein generally in relation to a pair of sample and reference beam paths 78,80.

Figure 14:
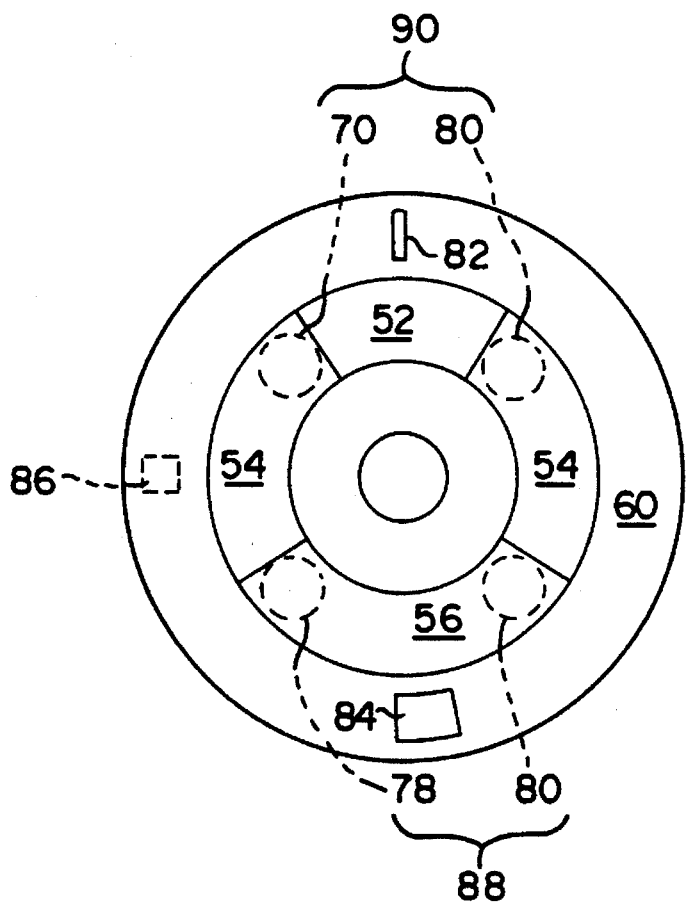
FIG. 14 is a schematic view of the filter unit of a multiple sample spectrophotometer of the invention.

The invention is not limited to a single sample beam path 78 in association with a single reference beam path 80. Referring now to multiple sample spectrophotometer shown in FIG. 14, besides a primary beam path pair 88, spectrophotometric device 10 includes an additional beam path pair 90. Multiple beam path pairs can have individual reference beam paths 80 or can share one or more reference beam paths 80. Optical path system 18 is appropriately modified so that each beam path pair 78,80 has an optical path system equivalent to that shown in FIGS. 1 and 4. Light source, electronics 22, computing means 24, and output device 26 may, but need not also be duplicated. Each beam path pair 78,80 provides, in effect, a separate spectrophotometer 12.

Referring again to FIGS. 1 and 2, annular-shaped orientation section 60 has a registration segment or locator 84. Main member 50 has a reader 86 disposed in alignment with orientation section 60. Registration segment 84 is radially offset from filter unit portions 52,54,56. Registration segment 84 can take a variety of forms and is, in essence, a pair of discontinuities in filter unit 42, which are capable of detection by reader 86, which is responsive to the initiation and termination of the juxtapositioning of registration segment 84 and reader 86. Reader 86 provides a continuous registration signal, in the embodiments of the invention shown in the Figures, however, separate signals for initiation and termination of alignment with locator 84 could also be used. In a particular embodiment of the invention, reader 86 is a bar code reader and registration segment 84 is a readable code or segment embossed or otherwise formed on the surface of orientation section 60. Registration segment 84 has a known length in the direction of travel of filter unit, which is used to determine the rate of rotation of filter unit 42, as discussed below in detail.

Orientation section 60 can include one or more other locators 82, if desired to indicate a "home" position or the like. The relative positions of locator 82 and registration segment 84 on orientation section 60 can be varied as desired, however, it is convenient, in an embodiment of the invention in which the beam paths are disposed 180 degrees apart, if locator 82 indicates the onset of filtration of one of the beams and the termination of registration segment 84 indicates the onset of filtration of the other beam.

Referring now to FIG. 2, in a particular embodiment of the invention, filter unit 42 also carries information. It is particularly convenient to provide one or more optically readable bar codes 85 or the like on orientation section 60, which are distinguishable from locator 82 and registration segment 84. Bar code 85 can provide information identifying the spectrophotometer in use and this information can be displayed with the output.

Reader 86, locator and registration segment can comprise a suitable number of energy emitters and detectors and the like. For example locator and registration segment can be slots or reflective portions on filter unit 42 that periodically allow the energy of an emitter to reach and not reach a detector.

Figure 3:
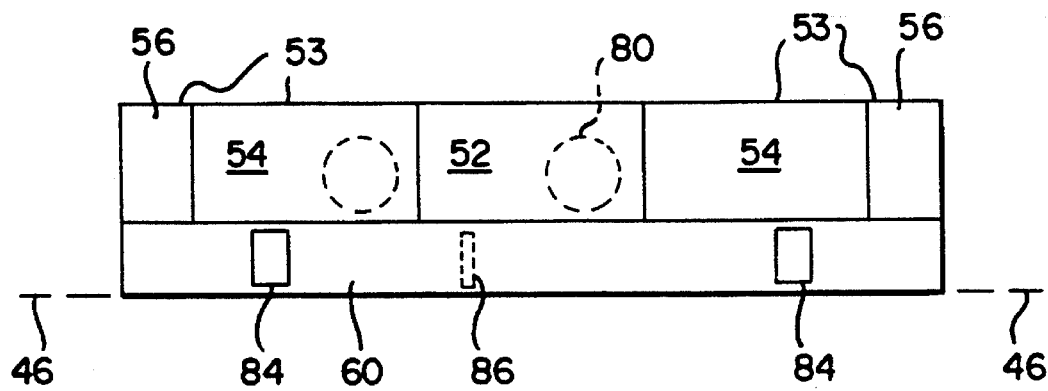
FIG. 3 is a schematic section view of an alternative embodiment of the spectrophotometer of the invention corresponding to the view of FIG. 2. The sample and reference beam paths and reader are indicated by dashed lines.

It is not necessary that the filter unit 42 of spectrophotometric device 10 be rotated. FIG. 3, shows a spectrophotometric device having a filter unit 42 that is reciprocated. Filter unit 42 has a longitudinal axis 46. Filter unit portions 52,54,56 extend longitudinally along axis 46 and have a width or maximum offset from axis 46 sufficient to accommodate beam paths 78,80. The main member, which is indicated only by the positions of beam paths 78,80 and reader 86 move relative to filter unit 42, forward and back along axis 46. Which of filter unit 42 and main member is fixed and which reciprocates is a matter of design choice for one skilled in the art, as is selection of an appropriate motor. As in rotating embodiments of the invention, multiple pairs of beam paths 78,80 can be used.

In the linear embodiment of the invention, shown in FIG. 3, a locator 82 is not present, but there are two registration segments 84. The two segments 84 are used to calibrate the reciprocation rate in respective directions. Reciprocation rates in the two directions can differ if desired, for example to provide a relatively slow scan of an unknown, varying sample and a relatively fast scan of a known, unchanging reference.

Suitable detector 20, computing means 24 and output device 26 are well known to those skilled in the art. Electronics 22 is shown schematically in FIG. 3A. Electrical components are conventional and should be designed for optimum signal-to-noise ratios. Electronics 22 are described below for a particular embodiment of the invention.

Figure 3A:
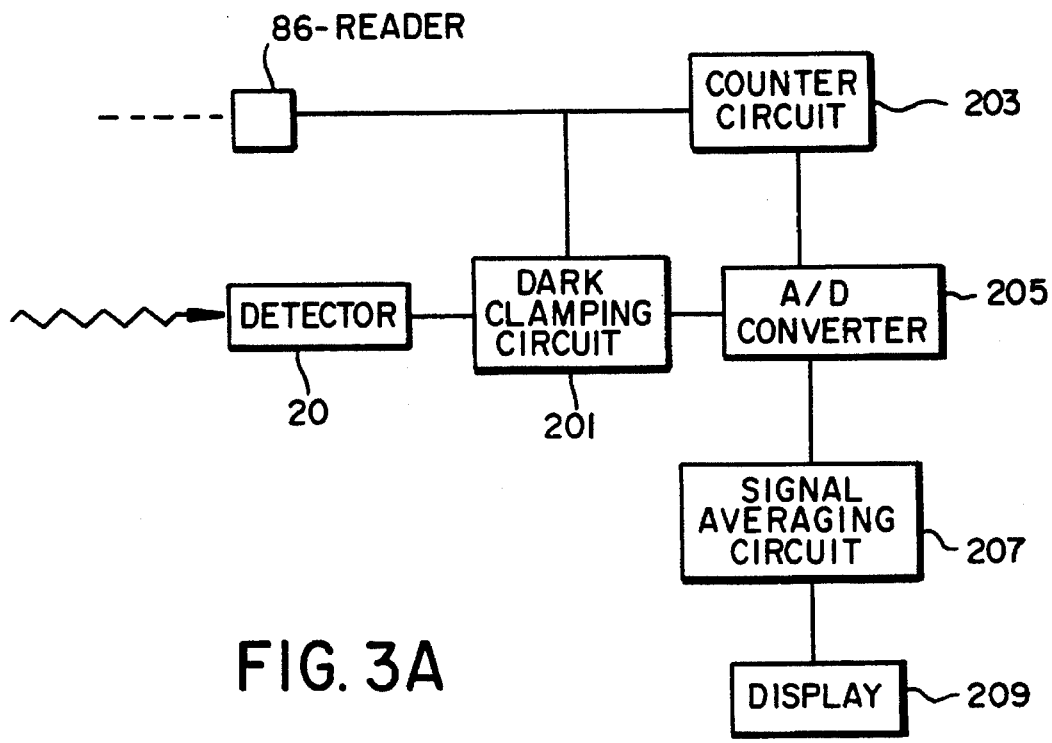
FIG. 3A is a schematic view of the electronics of the spectrophotometer of FIG. 1.

Referring now to FIG. 3A, detector 20, which can include an amplifier (not shown) sends a signal to dark clamping circuit 201. Reader 86 sends a registration signal to dark clamping circuit 201 and to a counter-timer 203 during alignment of registration segment 84.

Dark clamping circuit 201, is a conventional DC restorer clamping circuit. During a registration signal, clamping circuit 201 sets a restoration voltage at the same level as the signal provided by detector 20. This restoration or "dark" level represents the signal originating in detector 20 when both beam paths 78,80 are blocked, that is, when filter unit 42 and beam paths 78,80 are in "dark relation". In the absence of registration signal, that is, when a beam is transmitted through filtering portion 52 along one of beam paths 78,80, clamping circuit 201 clamps the detector signal to the restoration voltage. In other words, each light pulse in the detector signal is dark clamped to a restoration level set by the preceding dark pulse. The dark clamping compensates for dark current and for extraneous signals. The very short delay between setting the restoration level and dark clamping the succeeding light pulse, reduces the effect of variability in detector 20 and related circuitry.

Counter circuit 203 starts counting at the leading edge or initiation of a registration signal, and stops at the trailing edge or termination of the registration signal. The number of counts divided by the count rate equals the duration of the registration signal. Since the registration segment 84 that generates the registration signal has a known length in the direction of movement of filter unit 42 relative to the dimensions of filter unit 42 in the same direction, the rate of rotation or reciprocation of filter unit 42 can be calculated. Based upon that calculation, counter circuit 203 sends a rate of rotation signal to a analog-to-digital converter 205.

The analog-to-digital converter 205 receives the clamped detector signal from the dark clamping circuit 201 and a rate of rotation signal from the counter circuit 203. The analog-to-digital converter 205 has a variable sample acquisition rate, which is reset by the rate of rotation signal so as to provide a fixed number of data points during each cycle of filter unit 42. The output of analog-to-digital converter 205 is sent to a signal averaging circuit 207, which in turn sends an output to a display 209 or the like. Because the analog-to-digital converter output has a fixed number of data points, signal averaging is conveniently provided over any number of filter unit cycles.

In a particular embodiment of the invention, the electronics 22 utilize a voltage controlled oscillator, sold as part AD650KN by Analog Devices, Inc. of Norwood, Mass., which converts voltage pulses into frequency pulses that are then input to a counter-timer sold as part JDR 8254 by Intel Corp. of Santa Clara, Calif. Both units are controlled by a programmable processor board sold as Micromint RTC-V25 V25 by Micromint, Inc. of Vernon, Conn.

Figure 15:
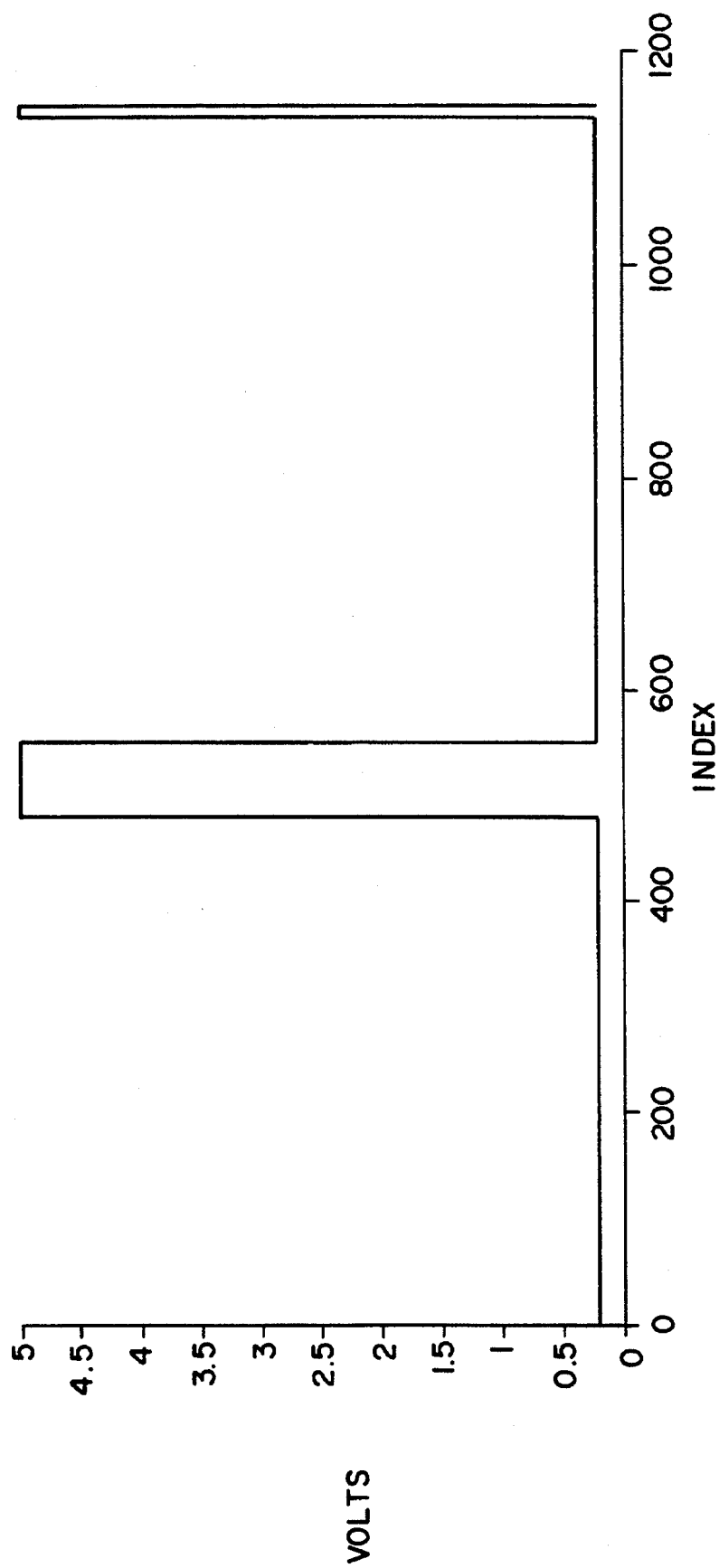
FIG. 15 is a schematic illustration of the output of the reader.
Figure 18:
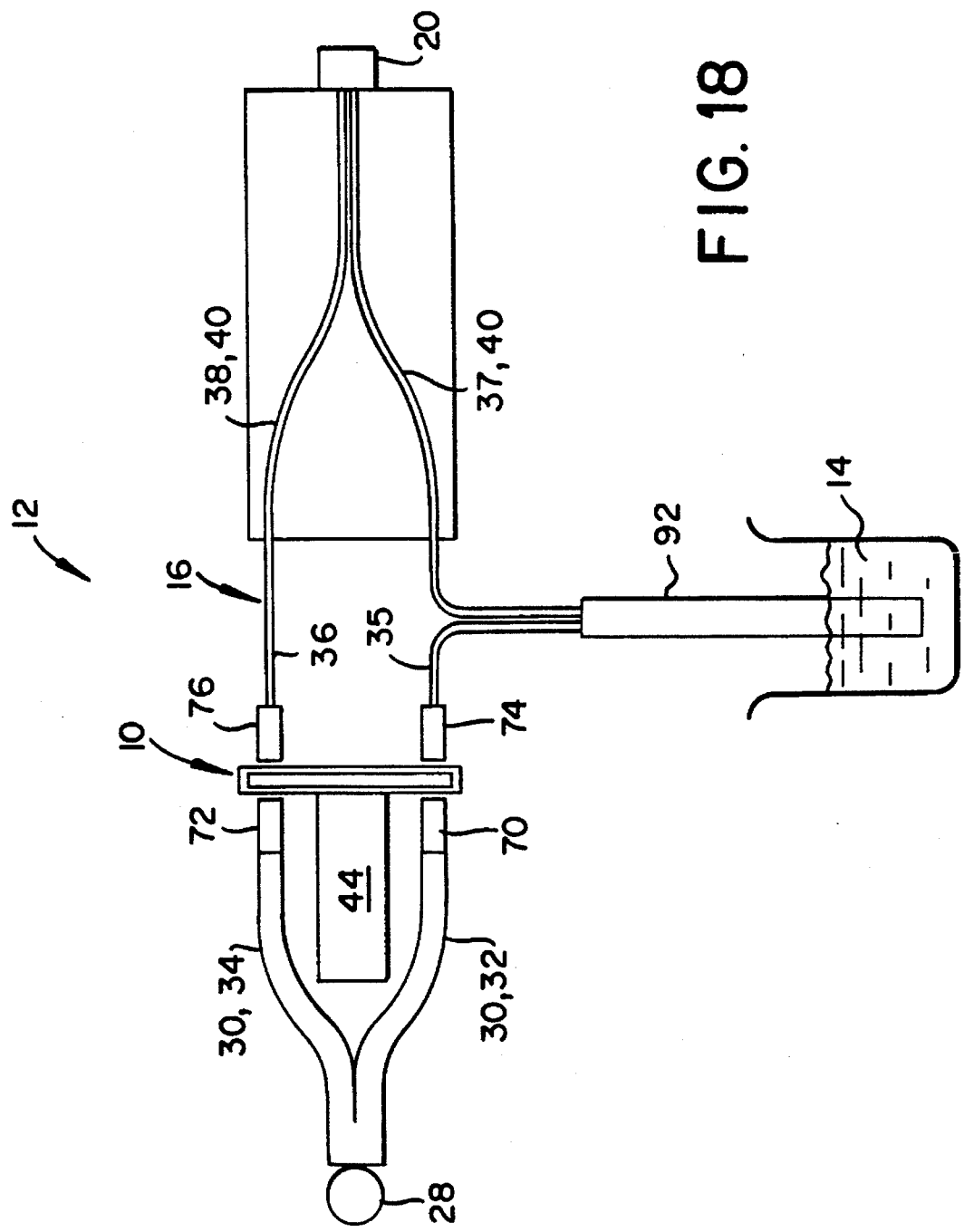
FIG. 18 is a schematic illustration of another embodiment of the spectrophotometer of the invention, in use, with a probe disposed in a liquid filled container.

In a particular embodiment of the invention, which is shown in FIG. 18, reader 86 provides the output shown in FIG. 15, in which volts are indicated on the vertical scale and a time based index having arbitrary units is used as the horizontal scale. The pulse due to locator 82 appears near the right-hand limit because the computer was triggered on the trailing edge of the pulse. The large pulse between index numbers 470 and 540 is due to registration segment 84 and can be used to adjust the data acquisition rate of the computer until this pulse appears precisely between specified index numbers. If it is desirable to maintain a constant data acquisition rate, then motor speed can be varied to adjust the length of the registration segment pulse.

Figure 16:
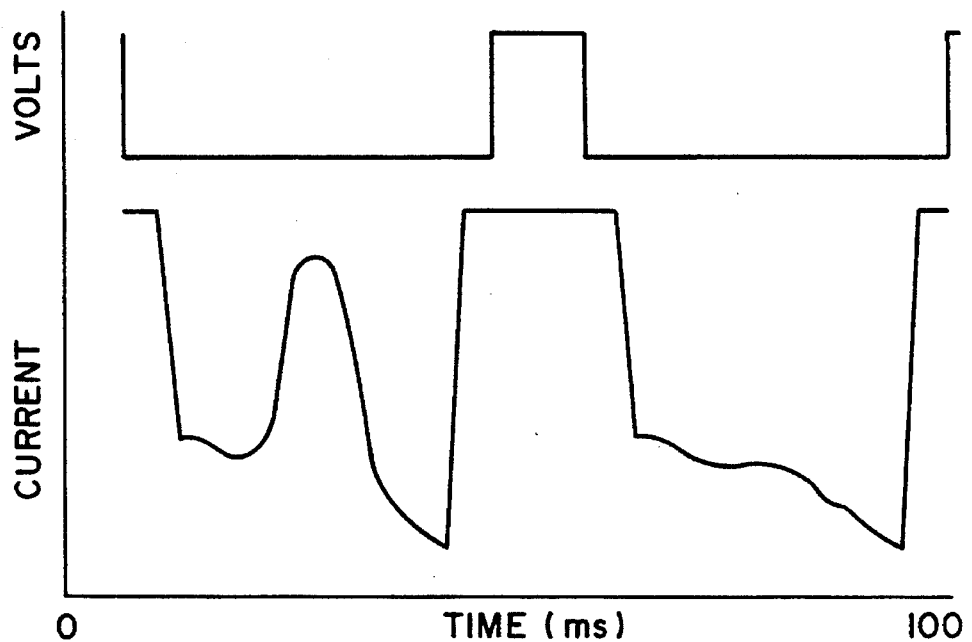
FIG. 16 is a schematic illustration of the output of the reader and the detector.
Figure 17:
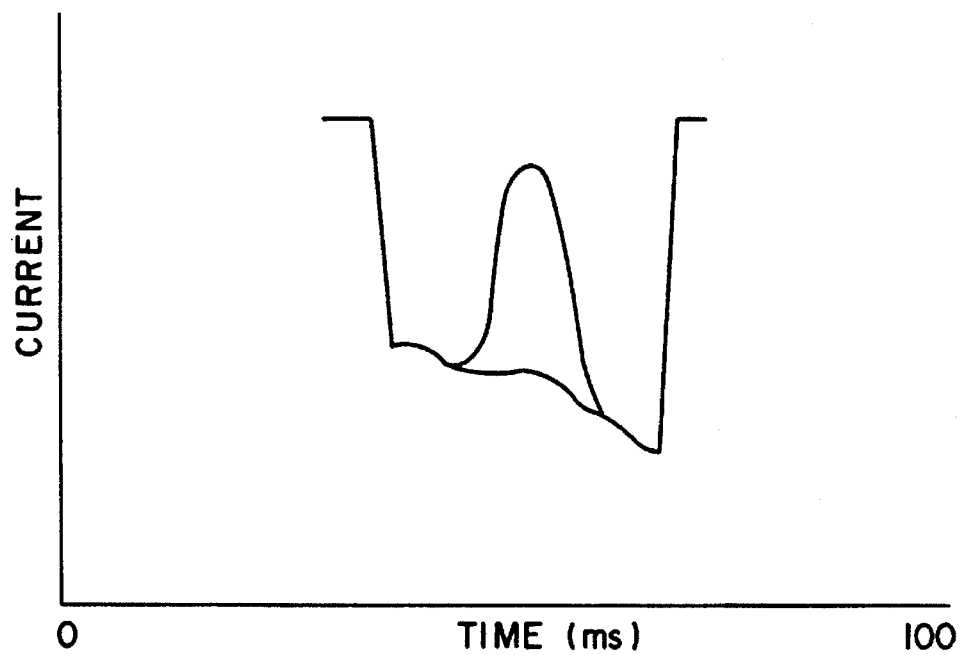
FIG. 17 is a schematic of a sample reading derived from the output presented in FIG. 16.

Referring now to FIG. 16, the diagram of FIG. 15, with a condensed voltage scale, is drawn above a graph of the output of detector 20, in which current is on the y-axis and time is on the x-axis. In this embodiment, the initiation of scanning of registration segment 84 by reader 86 coincides with the interruption of both beam paths 78,80 by opaque portion 53. Two response curves are shown, one on each side of the registration segment pulse. The number of data points incorporated in each curve can be the same on each side of the registration segment pulse or can differ, since the rotation rate (or rate of linear travel) is known from reader readings and the x-axis of each curve can be adjusted to compensate for variations in rotation speed. Phase shifting of curves due to rotation rate variations is accommodated at the same time. Since the two response curves have the same time scale, they can be combined to provide an indication of absorption solely due to the sample, as shown in FIG. 17. Interpolation will be required if the number of data points incorporated in each curve differ.

It will be readily appreciated that, by a comparison of the sample signal against the reference signal, a determination can be made, using conventional mathematics, of the presence (and amount) of certain materials that are present at the sample 14. Most importantly, this is accomplished with a single light source 28 and detector 20 per each beam path pair 78,80 to minimize drift; and optics to include a reference reading; and only one moving part (filter unit 42) to minimize breakdowns. By having the reference 16 be read very close in time to the sample read, e.g. within a few milliseconds for filter unit 42 being rotated at 1500 RPM, The potential for drift is further minimized.

In an alternative embodiment of the invention, an analog-to-digital converter utilizes a variable number of data points and the rate of rotation signal is used to scale a curve generated by the data points. Scaled curves can then be averaged. This approach is not favored since curve fitting and interpolation are be required.

It will be appreciated that the aforedescribed spectrophotometer 12 can be constructed without any mirrors or lenses being present. This provides the advantage of ruggedness and absence of alignment problems that otherwise occur.

FIG. 18 shows an exemplary, non-limiting example of a spectrophotometer 12 of the invention. In FIG. 18 and the other figures, identical reference numbers refer to like components of different embodiments. In this spectrophotometer 12, fiber 38 acts as a reference and fibers 35,37 are fixed in an optical probe 92. Example of component parts useful in the construction of the spectrometer of FIG. 18 are:

Light source: Tungsten-halogen lamp, 12 volt, 18 watt with flame formed lens;

Bifurcated fiber bundle: Industrial light guide, 0.002 inch fibers, common end-0.125 inch diameter bundle, branches-0.088 inch diameter bundles, random split of common end;

Motor: DC servo; GRIN lense

Reference fiber: telecommunication fiber, 100/140; Single Wand Fiber Probe: probe has a 500 micron fiber, 1 cm. pathlength using rhodium plated gold tip;

Bifurcated detector fiber assembly: uses Low OH fiber (FIP 500/550/590), detector end has two fibers mounted adjacent to each other in a single connector, leg ends each have a single fiber and are terminated with standard 905 SMA connectors;

Detector: duplex Si/Ge, 2 mm active area.

One skilled in the art can readily prepare the spectrophotometer of FIG. 20 from the components listed in the Example. Other types of spectrophotometer can also be readily prepared. For example, to practice resonance Raman spectroscopy, light source would be chosen to have wavelengths that are in resonance with electronic transitions of the analyte of interest. Pass-through filters would be chosen as for standard Raman spectroscopy, but the intensity may be much higher at the detected bands, allowing for better signal at the detector. For surface enhanced Raman spectroscopy the sample would be prepared to enhance Raman signals from an analyte. Appropriate sample surfaces are well known to those skilled in the art, and can include electrochemically roughened metal electrodes, metal colloids and sols, metal island films, and the like.

The invention has been described in detail with particular reference to preferred embodiments thereof, but it will be understood that variations and modifications can be effected within the spirit and scope of the invention.

What is claimed is:

1. A variable filter spectrophotometer for use with a sample and a reference, comprising:
   a main member defining first and second beam paths,
   a filter unit intersecting said beam paths, said filter unit having a filtering portion and an opaque portion, said filter unit being continuously movable relative to said beam paths in a repeating cycle from a first filtering relation wherein said filtering portion is interposed in said first beam path and said opaque portion completely blocks said second beam path, then to a first dark relation wherein both said beam paths are blocked, then to a second filtering relation wherein said filtering portion is interposed in said second beam path and said first beam path is completely blocked, and then to a second dark relation wherein both said beam paths are completely blocked, said filtering portion being variably transmissive to selected wavelengths of light along a direction of said movement of said filter unit, said opaque portion being at least substantially opaque to said selected wavelengths of light transmittable by said filtering portion,
   a drive for continuously moving said filter unit relative to said beam paths,
   a detector for producing a signal responsive to light received,
   a light distribution system directing light separately to and from said sample and reference, to and from said beam paths, and to said detector, and
   means for clamping said signal produced by said detector during said filtering relations to the signal produced by said detector during said dark relations.

2. The spectrophotometer of claim 1 wherein said beam paths each have a periphery and said filtering portion has a maximum dimension in a direction of said movement of said filter unit less than the minimum periphery to periphery separation of said beam paths in the same direction.

3. The spectrophotometer of claim 1 further comprising means for allotting said detector signal to individual said cycles of said movement of said filter unit, and means for averaging said allotted detector signal over a number of said cycles, said means for averaging including means for determining the rate of movement of said filter unit during each said cycle.

4. The spectrophotometer of claim 3 further comprising a clamping circuit, said clamping circuit setting a restoration signal proportional to said detector signal when said filter unit and said beam paths are in each said dark relation, said clamping circuit clamping said detector signal to said restoration signal when said filter unit and said beam paths are in each said filtering relation.

5. The spectrophotometer of claim 3 wherein said filter unit has a registration segment having a predetermined dimension in a direction of said movement of said filter unit, and said main member has a reader, said registration segment moving past said reader during each said cycle, said reader being responsive to initiation and termination of alignment of said registration segment and said reader.

6. The spectrophotometer of claim 5 whereto said filter unit carries optically readable information and said reader further comprises means for reading said information.

7. The spectophotometric device of claim 6 wherein said reader is a bar code reader and said information is in bar code form.

8. The spectrophotometer of claim 1 wherein said filter unit has a registration segment having a predetermined dimension in a direction of said movement of said filter unit, said dimension being less than the maximum dimension of said filter unit in the same direction, and said main member has a reader, said registration segment moving past said reader during each said cycle, said reader being responsive to initiation and termination of alignment of said registration segment and said reader.

9. The spectrophotometer of claim 1 wherein said filter unit carries optically readable information.

10. The spectrophotometer of claim 1 wherein said main member defines an axis of movement and said filter unit is rotated about said axis by said drive.

11. The spectrophotometer of claim 1 wherein said main member defines an axis of movement and said filter unit is reciprocated along said axis by said drive.

12. The spectrophotometer of claim 11 wherein said filter unit is moved at different speeds through said first and second beam paths.

13. The spectrophotometer of claim 1 wherein said main member defines a plurality of pairs of said first and second beam paths.

14. The spectrophotometer of claim 13 wherein said beam paths each have a periphery and said filtering portion has a maximum dimension in a direction of said movement of said filter unit less than the minimum periphery to periphery separation of said beam paths in the same direction.

15. The spectrophotometer of claim 1 wherein said filter unit further comprises a unitary filter disk having a hemicircular filter arc and a hemicircular opaque arc, and a shell rendering opaque part of said filter arc.

16. A variable filter spectrophotometer comprising a main member having a pair of beam paths and an axis, said beam paths being disposed in uniform relation to said axis, said beam paths each having a periphery, a filter unit interposed in said beam paths, said filter unit being coaxial with said main member, said filter unit having filtering, blocking, and dark portions, said filter unit being continuously movable relative to said axis to move said filter unit portions through said beam paths, said filtering portion being variably transmissive to selected wavelengths of light along a direction of said movement of said filter unit, said blocking and dark portions being at least substantially opaque to said light transmittable by said filtering portion, said filtering portion having a maximum dimension in a direction of movement of said filter unit less than the minimum separation of said beam path peripheries, said blocking portion completely blocking one said beam paths continuously during the movement of said filtering portion through the other said beam path, said dark portion simultaneously interposable in both said beam paths.

17. The spectrophotometer of claim 16 wherein said main member has a plurality of said beam path pairs.

18. The spectrophotometer of claim 16 wherein said filter unit has an orientation section disposed relative to said axis at an offset from said filtering, blocking and dark portions, said orientation section having a locator and a registration segment, said registration segment having a predetermined dimension in a direction of said movement of said filter unit, said main member having a reader disposed in alignment with said orientation section, said reader being responsive to the juxtapositioning of said locator and said reader and to the initiation and termination of juxtapositioning of said registration segment and said reader.

19. The spectrophotometer of claim 16 wherein said filter unit has a longitudinal axis, and said filter unit portions extend longitudinally along said filter unit axis.

* * * * *